(12) United States Patent
Schön

(10) Patent No.: US 10,379,387 B2
(45) Date of Patent: Aug. 13, 2019

(54) METHOD AND DEVICE FOR CHECKING REFRACTIVE POWER DISTRIBUTION AND CENTERING

(71) Applicant: Carl Zeiss Vision International GmbH, Aalen (DE)

(72) Inventor: Roland Schön, Aalen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 15/961,653

(22) Filed: Apr. 24, 2018

(65) Prior Publication Data

US 2018/0239174 A1    Aug. 23, 2018

Related U.S. Application Data

(63) Continuation of application No. PCT/EP2016/075592, filed on Oct. 25, 2016.

(30) Foreign Application Priority Data

Oct. 27, 2015   (DE) .................. 10 2015 220 931

(51) Int. Cl.
*A61B 3/10* (2006.01)
*G02C 13/00* (2006.01)
(Continued)

(52) U.S. Cl.
CPC .............. *G02C 13/005* (2013.01); *A61B 3/04* (2013.01); *G01M 11/0214* (2013.01);
(Continued)

(58) Field of Classification Search
CPC ............................ A61B 3/111; A61B 3/112
(Continued)

(56) References Cited

U.S. PATENT DOCUMENTS 5,855,074 A    1/1999 Abitbol et al.
7,422,325 B2   9/2008 Kaga
(Continued)

FOREIGN PATENT DOCUMENTS

CN       1890596 A    1/2007
CN     101201464 A    6/2008
(Continued)

OTHER PUBLICATIONS

Office action issued by the Chinese Patent Office (SIPO) in patent application CN 201680063121.8, which is a counterpart application hereof, dated Sep. 21, 2018, and English-language translation thereof.

(Continued)

*Primary Examiner* — Hung X Dang
(74) *Attorney, Agent, or Firm* — Ewers & Hasselmann PLLC

(57) ABSTRACT

A device for checking the refractive power distribution and/or centering of a spectacle lens is disclosed. The device includes a holder for arranging the spectacle lens in a measuring position, a display device for displaying a test structure, and an image capture device for capturing an actual image of the test structure for an imaging beam passing through the spectacle lens arranged in the measurement position. The display device simultaneously displays the captured actual image and a target complement image complementary to a target image of the test structure, wherein the target image of the test structure is that image which would arise for an imaging beam passing through a spectacle lens, arranged in a predefined target measuring position, with a predefined target refractive power distribution. The corresponding method for checking the refractive power distribution and/or centering of a spectacle lens is also disclosed.

15 Claims, 3 Drawing Sheets

(51) Int. Cl.
*G01M 11/02* (2006.01)
*A61B 3/04* (2006.01)

(52) U.S. Cl.
CPC .... *G01M 11/0235* (2013.01); *G01M 11/0264* (2013.01); *G02C 13/003* (2013.01)

(58) Field of Classification Search
USPC .................................................. 351/204, 200
See application file for complete search history.

(56) References Cited

U.S. PATENT DOCUMENTS

| | | | |
|---|---|---|---|
| 7,508,502 B2 | 3/2009 | Divo et al. | |
| 7,631,969 B2 | 12/2009 | Shinohara et al. | |
| 9,022,565 B2 | 5/2015 | Sauer et al. | |
| 9,645,043 B2 | 5/2017 | Allione | |
| 2007/0115353 A1 | 5/2007 | Divo et al. | |
| 2011/0317127 A1 | 12/2011 | Suzuki et al. | |
| 2015/0300912 A1 | 10/2015 | Allione | |
| 2016/0011437 A1* | 1/2016 | Nishimura | G02C 7/027 351/204 |

FOREIGN PATENT DOCUMENTS

| | | |
|---|---|---|
| CN | 101382667 A | 3/2009 |
| CN | 102314001 A | 1/2012 |
| CN | 104870967 A | 8/2015 |
| DE | 10 2008 039 416 A1 | 2/2010 |
| DE | 10 2015 211 879 A1 | 12/2016 |

OTHER PUBLICATIONS

Office action issued by the German Patent and Trademark Office (DPMA) in patent application DE 10 2015 220 931.8, to which this application claims priority, dated Nov. 3, 2016, and English-language translation thereof.

Office action issued by the Israel Patent Office (ILPO) in patent application IL 258797, which is a counterpart of this application, dated Aug. 13, 2018, and English-language translation thereof.

Office action issued by the Korean Patent Office (KIPO) in patent application KR 10-2018-7014202, which is a counterpart of this application, dated Aug. 17, 2018, and English-language translation thereof.

International Preliminary Examination Report issued in PCT/EP2016/075592, to which this application claims priority, dated Mar. 6, 2018, and English-language translation thereof.

International Search Report and English-language translation thereof issued in PCT/EP2016/075592, of which this application is a continuation application, dated Feb. 8, 2017.

* cited by examiner

METHOD AND DEVICE FOR CHECKING REFRACTIVE POWER DISTRIBUTION AND CENTERING

CROSS REFERENCE TO RELATED APPLICATIONS

This application is a continuation application of International patent application PCT/EP2016/075592, filed Oct. 25, 2016, and claims priority to German patent application DE 10 2015 220 931.8 filed on Oct. 27, 2015, both of which are hereby incorporated by reference in their entireties.

TECHNICAL FIELD

The disclosure relates to a method for checking the refractive power distribution or for inspecting the optical power and/or the centering of a spectacle lens, and to a device for checking the refractive power distribution and/or the centering of a spectacle lens. In this context, centering is understood to mean the correct incorporation of spectacle lenses into a spectacle frame taking account of the position and the correct alignment with respect to the pupil distance of the wearer of the spectacles.

BACKGROUND

A method and a device for checking the centering of spectacle lenses mounted into a spectacle frame are described in U.S. Pat. No. 9,022,565 B2. The method involves firstly determining the positions of permanent markings in the spectacle lenses relative to the frame. The setpoint centering points on the spectacle lenses are determined from the positions determined. Actual centering points for the wearer of the spectacles are determined with the aid of a video centering device. Actual and setpoint centering points are then compared with one another. Accordingly, this method involves checking (possibly automatically) the position of the spectacle lenses seated by grinding on the basis of the permanent engravings. This method functions only in the case of spectacle lenses on which such permanent engravings are also present.

DE 10 2015 211 879 A1, from which the disclosure proceeds, describes a device and a method for measuring the refractive power distribution of a spectacle lens of spectacles arranged in a measurement position. In the method, the spectacles are arranged in a measurement position. A test structure is then provided. The imaging of the test structure is then captured by way of an imaging beam path which passes through one of the spectacle lenses of the spectacles arranged in the measurement position. The refractive power distribution of the spectacle lens is then determined from the coordinates of the test structure and the captured imaging of the test structure and from the spatial position of the spectacle lens relative to the test structure or the imaging of the test structure. This method is also suitable for measuring spectacle lenses without permanent engravings.

Although both the above-described methods and arrangements have basically proved worthwhile, there is a need for a simple means for process control.

SUMMARY

It is an object of the disclosure to provide a method and a device suitable for control of the seating by a grinding process, and, typically, to ensure universal usability.

This object is achieved by a method and a device as disclosed herein.

The method according to the disclosure for checking the refractive power distribution and/or the centering of a spectacle lens includes:
arranging the spectacle lens in a measurement position,
providing a test structure,
capturing an actual imaging of the test structure for an imaging beam which passes through the spectacle lens arranged in the measurement position, and
alternatively
comparing the captured actual imaging with a calculated setpoint imaging of the test structure which would arise for an imaging beam which would pass through a spectacle lens arranged in a predefined setpoint measurement position with a predefined setpoint refractive power distribution, or
comparing the captured actual imaging with a setpoint complement imaging complementary to a setpoint imaging of the test structure, wherein the setpoint imaging of the test structure is that imaging which would arise for an imaging beam which would pass through a spectacle lens arranged in a predefined setpoint measurement position with a predefined setpoint refractive power distribution.

The method presupposes that setpoint values are present for the properties to be checked, i.e., it serves to perform a setpoint-actual comparison in the context of process control.

It is expedient if the test structure is calculated from the predefined setpoint imaging. This is because in this case a comparatively simple geometric structure, namely a known symbol or a frequently used sign, e.g., a circular ring, a regular grid network or the like, can be predefined as setpoint imaging, with the result that deviations of the actual imaging from the geometry are able to be ascertained rapidly.

The test structure can be calculated from the predefined setpoint imaging, e.g., by a light ray tracing method. Methods of this type are customary for the calculation of optical elements, and so all that is needed is an adaptation, in particular a reversal of the computation path, of the equipment that is customary anyway.

In principle, it is possible to use the method for spectacle lenses which have experienced a change with regard to a standard, in order to ascertain qualitatively whether the desired change that has been made tends to exhibit the desired result. However, it is also possible to check comparatively exactly even individually adapted spectacle lenses with regard to refractive power distribution and/or centering. In this case, it is necessary to determine for each individual case a setpoint refractive power distribution corresponding to the refractive power distribution which the spectacle lens to be checked should have computationally on account of the design data on which its production is based.

Since knowledge of the spatial positional relation between actual measurement position and setpoint measurement position is important for the accuracy of the comparison, it is expedient to be able to define and/or determine both the actual measurement position and the setpoint measurement position as accurately as possible. The disclosure therefore provides for calculating the predefined setpoint measurement position from centering parameters, in particular the coordinates of the centering point, of the spectacle lens to be checked.

A comparison of the actual imaging and the setpoint imaging can be carried out in a wide variety of ways. It is, e.g., possible to predefine a non-variable setpoint imaging standard arranged in the vicinity of the checking apparatus. It is also possible not to display actual imaging and setpoint imaging at all, but rather to carry out a computational comparison with a computer. Calculations of this type can be computationally intensive and hence time-intensive under certain circumstances. A visual approach includes simultaneously displaying the actual imaging and the setpoint imaging. Alternatively, the actual imaging and the setpoint complement imaging can also be displayed simultaneously. This enables a checking person to take a decision about the quality of the actual refractive power distribution and/or the centering of the tested spectacle lens.

It is possible to display the actual imaging and the setpoint imaging alongside one another for carrying out the comparison. The accuracy is generally increased, however, if the actual imaging and the setpoint imaging are displayed in a manner superimposed on one another, or if the actual imaging and the setpoint complement imaging are displayed in a manner superimposed on one another.

The accuracy when carrying out the comparison with superimposed representation is particularly high if the actual imaging and the setpoint imaging are displayed in a manner brought to congruence or if the actual imaging and the setpoint complement imaging are displayed complementarily with respect to one another.

A corresponding device according to the disclosure for checking the refractive power distribution and/or the centering of a spectacle lens comprises the following component parts:

a holder for arranging the spectacle lens in a measurement position,
   a display unit for displaying a test structure,
   an image capture unit for capturing an actual imaging of the test structure for an imaging beam which passes through the spectacle lens arranged in the measurement position, and optionally
   a comparison unit for comparing the captured actual imaging with a setpoint imaging of the test structure, wherein the setpoint imaging of the test structure is that imaging which would arise for an imaging beam which would pass through a spectacle lens arranged in a predefined setpoint measurement position with a predefined setpoint refractive power distribution, or for comparing the captured actual imaging with a setpoint complement imaging complementary to a setpoint imaging of the test structure, wherein the setpoint imaging of the test structure is that imaging which would arise for an imaging beam which would pass through a spectacle lens arranged in a predefined setpoint measurement position with a predefined setpoint refractive power distribution; or
   a display unit for simultaneously displaying the captured actual imaging and a setpoint imaging of the test structure, wherein the setpoint imaging of the test structure is that imaging which would arise for an imaging beam which would pass through a spectacle lens arranged in a predefined setpoint measurement position with a predefined setpoint refractive power distribution, or for simultaneously displaying the captured actual imaging and a setpoint complement imaging complementary to a setpoint imaging of the test structure, wherein the setpoint imaging of the test structure is that imaging which would arise for an imaging beam which would pass through a spectacle lens arranged in a predefined setpoint measurement position with a predefined setpoint refractive power distribution.

It was explained above that the accuracy of the comparison result is dependent on the actual and setpoint measurement positions. If the holder has holding points, the position of which in space is previously known, the spectacle lens to be checked or the spectacles comprising the spectacle lens to be checked can be brought comparatively simply into a predeterminable position (typically with regard to location and orientation).

It has been found to be expedient if the holder has a compensation unit for compensating for a forward inclination and/or a lateral inclination (of the spectacles comprising the spectacle lens to be checked). The compensation unit can include e.g., a tilting and/or rotating unit in order to tilt or rotate the spectacle lens or the spectacles comprising the spectacle lens in accordance with a corresponding predefinition. However, it is also possible for the compensation unit to allow a mounting of the spectacle lens or of the spectacles comprising the spectacle lens exclusively in a manner compensating for forward inclination and/or lateral inclination.

In an exemplary embodiment, the device includes a holder that is configured for holding spectacles, and the holder includes an interchange unit for sequentially checking the refractive power distribution and/or the centering of the right and left spectacle lenses of the spectacles. The interchange unit can be configured as manually operable or automated. The interchange unit can be distinguished, in particular, by the fact that it can bring the respective spectacle lenses into a predetermined or predeterminable position.

The device according to the disclosure can also comprise a displacement unit for relatively displacing the holder and the image capture unit with respect to one another, e.g., to correct a distorted or unsharp representation of the actual and/or setpoint imagings.

In a corresponding manner, the device can additionally or alternatively comprise a displacement unit for relatively displacing the holder and the display unit. The displacement unit, too, can serve to correct distorted or unsharp representations of the actual and/or setpoint imagings.

BRIEF DESCRIPTION OF THE DRAWINGS

The disclosure will now be described with reference to the drawings wherein.

DESCRIPTION OF EXEMPLARY EMBODIMENTS

Figure 1:
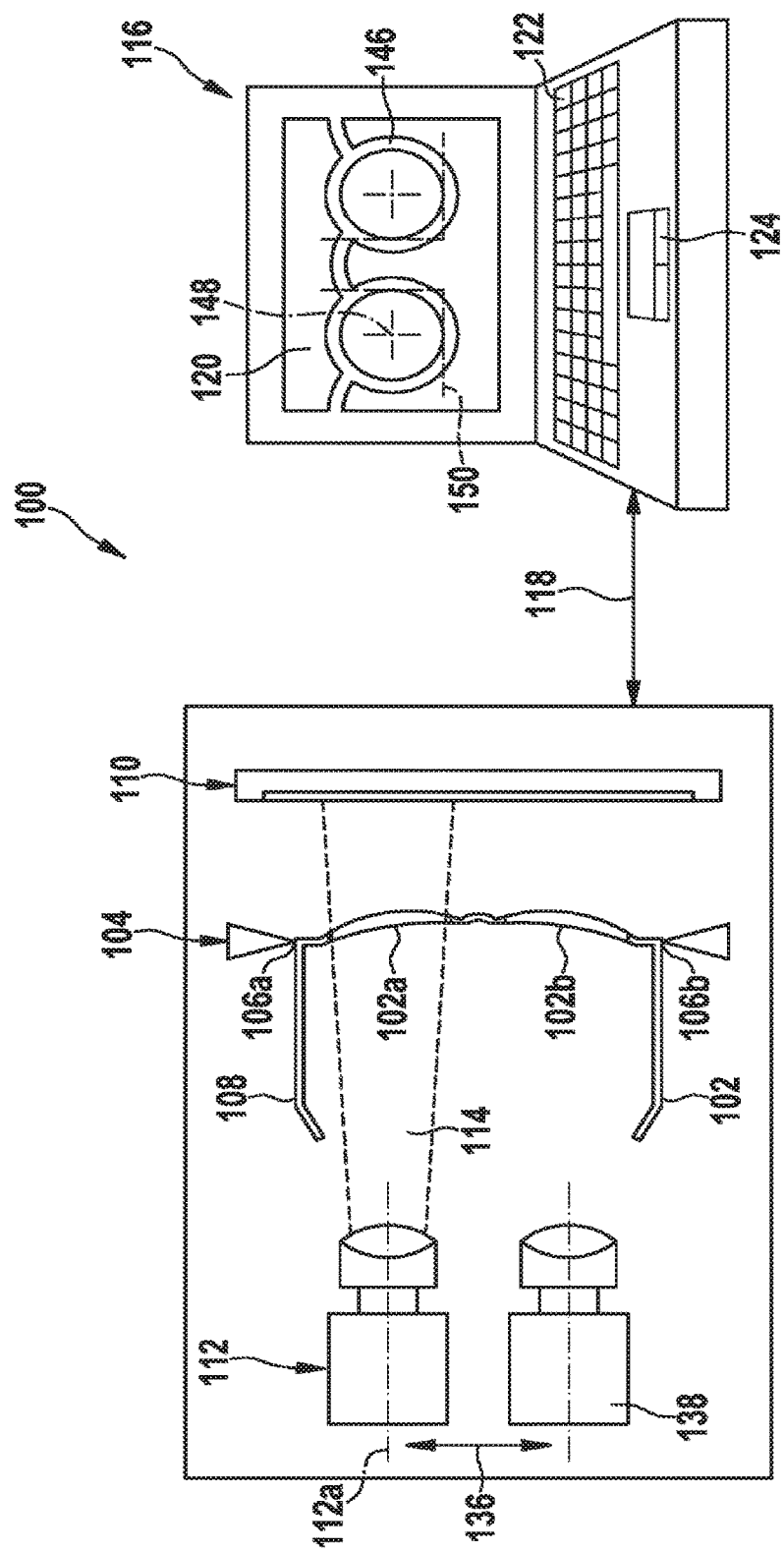
FIG. 1 shows an exemplary embodiment of a device for checking the refractive power distribution and/or the centering of a spectacle lens.

FIG. 1 shows an exemplary embodiment of a device 100 according to the disclosure for checking the refractive power distribution and/or the centering of a spectacle lens 102a. The device 100 comprises a holder 104 (depicted schematically with the aid of two holding points 106a, 106b), which holds spectacles 102 comprising two spectacle lenses 102a, 102b mounted in the frame 108 of the spectacles in a measurement position. Part of the device 100 is a screen 110, which serves as a display unit for displaying a test structure. A camera 112 is present as an image capture unit. The camera serves for capturing an actual imaging of the test structure displayed on the screen 110 which arises for an imaging beam 114 which emanates from the screen and which passes through the spectacle lens 102a arranged in the measurement position and impinges on the camera 112.

Part of the device 100 is a computer 116. The computer 116 serves for data recording, data processing, and control of screen 110, camera 112 and possibly holder 104 (cf. description below). The corresponding data link from the computer 116 to the screen 110, to the camera 112, and to the holder 104 is identified in the drawing by a double-headed arrow identified by the reference sign 118. A keyboard 122 having a touchpad 124 is present for operating the computer 116.

A further part of the device is an additional display unit, namely a screen 120, which belongs to the computer 116 in the present exemplary embodiment. The screen 120 serves to display the actual imaging of the test structure captured by the camera 112 and also simultaneously a setpoint imaging of the test structure or a setpoint complement imaging complementary to the setpoint imaging. In this case, a setpoint imaging of the test structure is that imaging which would arise for an imaging beam which would pass through a spectacle lens arranged in a predefined setpoint measurement position with a predefined setpoint refractive power distribution.

Figure 2A:
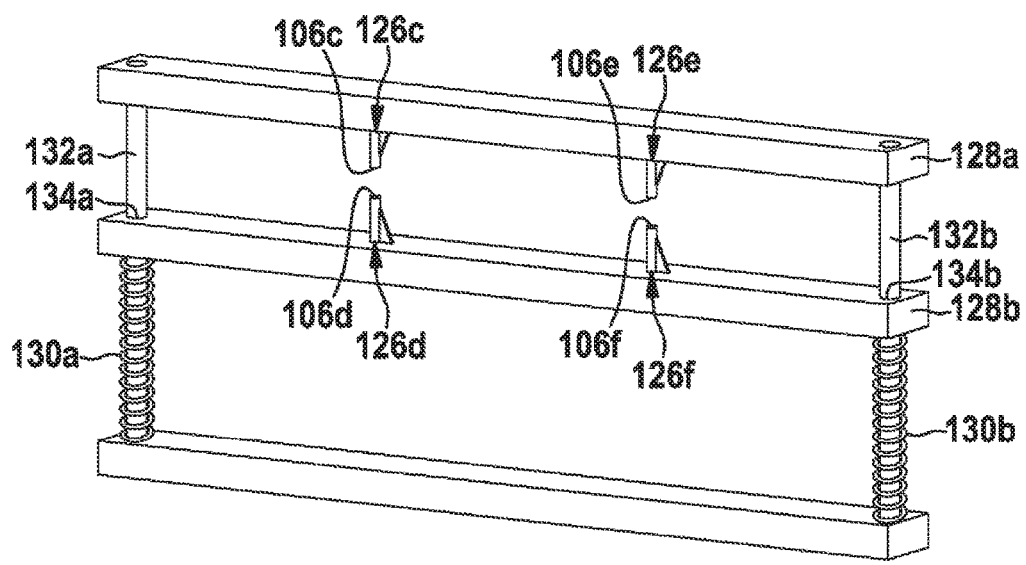
FIG. 2A shows a holder for spectacles which is suitable for use in the device according to FIG. 1.
Figure 2B:
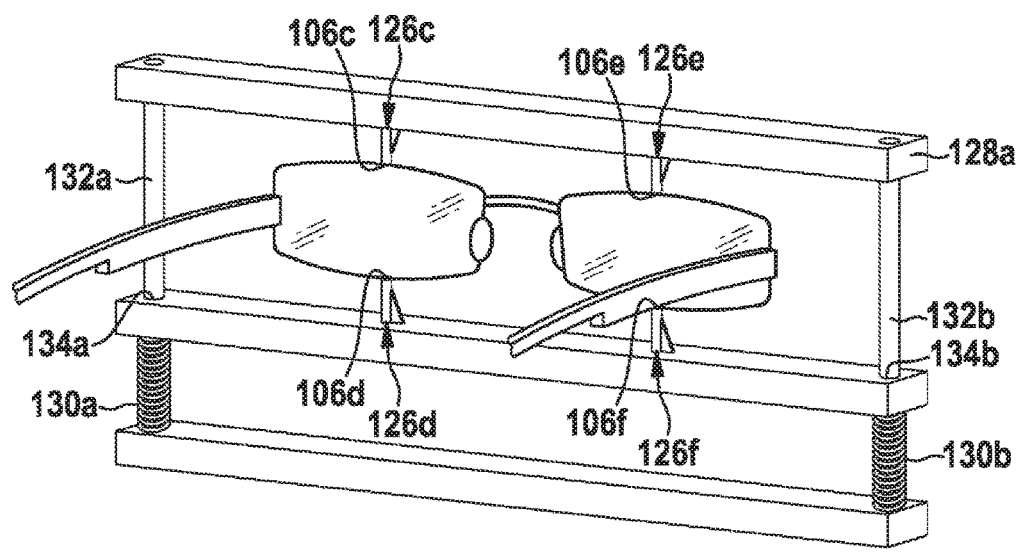
FIG. 2B shows the holder according to FIG. 2A with spectacles held by it.

One exemplary embodiment of a holder 104 is depicted in FIGS. 2A and 2B. FIG. 2A shows the holder 104 without spectacles; FIG. 2B shows the holder according to FIG. 2A with spectacles held by it. The holder 104 for the spectacles 102 as shown in FIGS. 2A and 2B has holding points 106c, 106d, 106e, 106f, the position of which in space is completely known, and, for spectacles 102 clamped in, the holder compensates for the forward inclination of the spectacle lenses 102a, 102b. The holding points 106c, 106d, 106e, 106f are the contact points of U-shaped receptacle elements 126c, 126d, 126e, 126f, two of which respectively are arranged opposite one another with their openings directed toward one another. The four U-shaped receptacle elements 126c, 126d, 126e, 126f are supported by two rods 128a, 128b arranged parallel to one another. The two rods 128a, 128b are held in each case at their ends by two supporting rods 132a, 132b. The upper rod 128a is fixedly connected to the two supporting rods 132a, 132b. The lower rod 128b has openings 134a, 134b in each case at its ends, through which openings the supporting rods 132a, 132b pass, with the result that the lower rod 128b is guided on the supporting rods 132a, 132b in a manner displaceable parallel to the upper rod 128a. The lower rod 128b can be displaced counter to the force of two helical springs 130a, 130b, through which the supporting rods 132a, 132b pass.

The holder 104 shown in FIGS. 2A and 2B allows a positionally defined arrangement (with regard to location and orientation) of spectacles in space without a possibility or need for readjustment. It may be helpful to provide an adjustment per se. In such a case, the holder is configured such that it is displaceable and also rotatable and pivotable in all spatial directions. A corresponding electronic control via the computer 116 is typical in this case. Furthermore, a camera-aided position detection unit is helpful.

To be able to check both the left spectacle lens and the right spectacle lens sequentially, either the camera 112 or the spectacles holder 104 is displaceable perpendicularly to the optical axis 112a of the camera 112 (direction arrow 136). Alternatively, it is also possible to employ two cameras 102, 138. In this case, both spectacle lenses 102a, 102b can be checked simultaneously.

Figure 3:
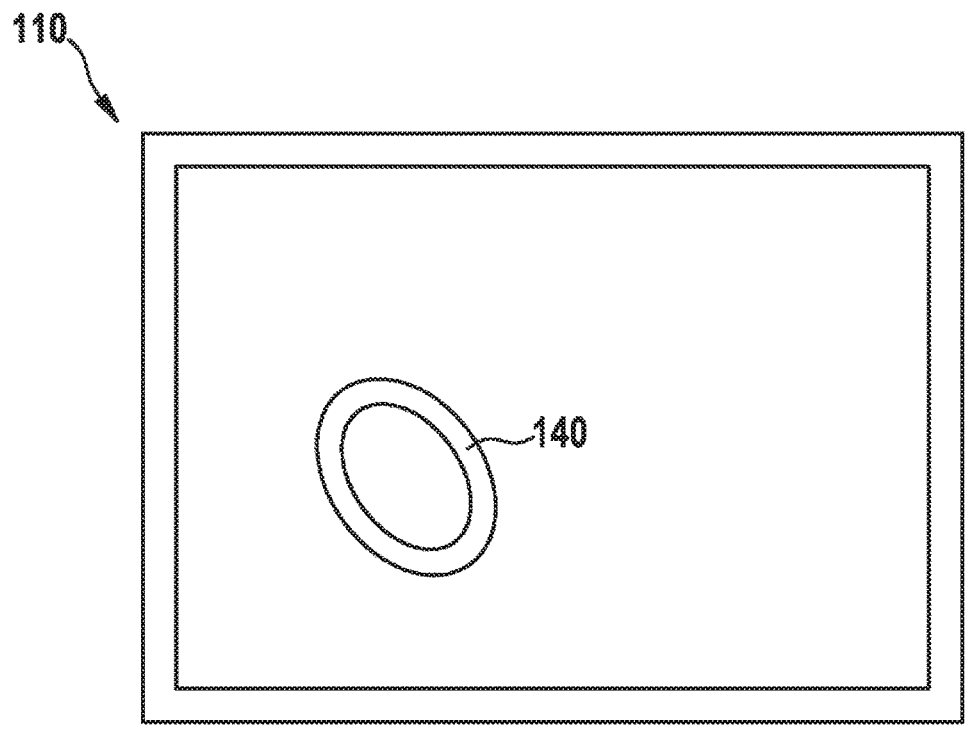
FIG. 3 shows a test structure in the form of an ellipse that is displayed by the screen of the device shown in FIG. 1.
Figure 4:
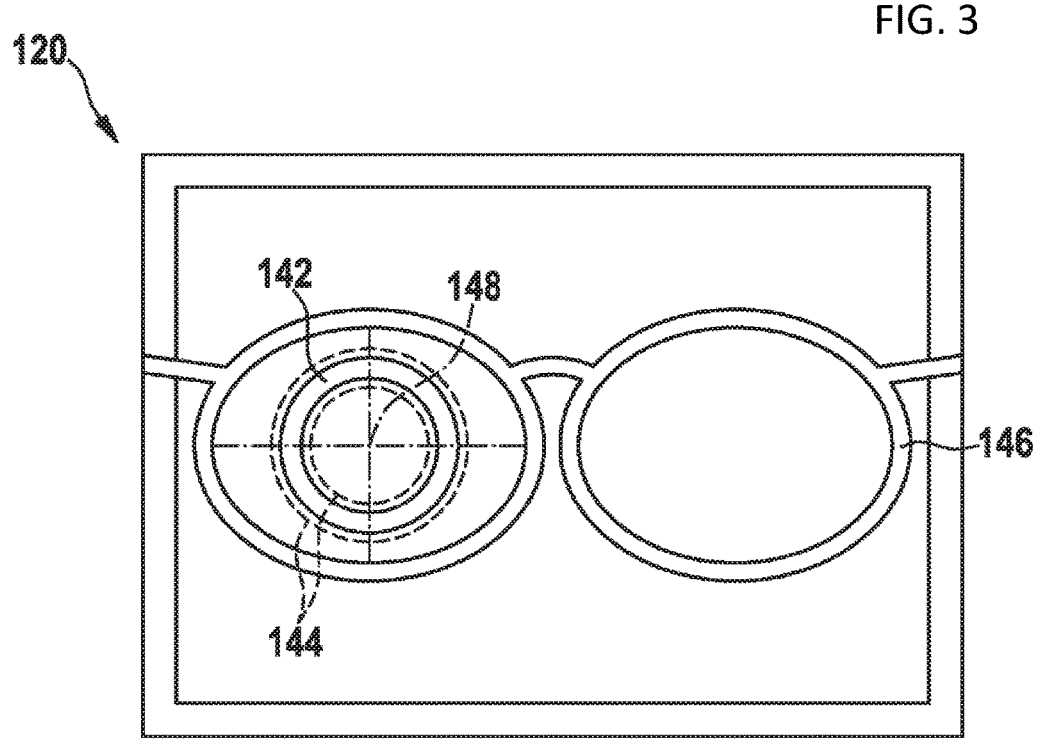
FIG. 4 shows the display of the computer screen of the device shown in FIG. 1 with actual imaging captured by the camera of the device shown in FIG. 1 and complementary setpoint complement imaging.

A test structure, e.g., an ellipse 140, calculated by a suitable algorithm, e.g., ray tracing, is displayed on the screen 110 (cf. FIG. 3). The test structure 140 is calculated such that it is imaged, as viewed by the camera 112 through the spectacle lens 102a of the spectacles 102, without distortion and at a defined location of the image sensor depending on the position of the optical center of the spectacle lens 102a. This actual imaging 142 is displayed on the screen 120 (FIG. 4).

The calculation of the test structure 140 to be displayed on the screen 110 requires the centering parameters and the refractive power (sphere, cylinder, axis, prism) of the spectacle lens 102a, which are transferred to the device 100 before a measurement. If the calculated test structure 140 is imaged by the camera 112 without distortion, at the correct position and with the correct size, then it can be assumed that the spectacle lens 102a was seated with the correct refractive power and the correct centering. If deviations from the expected image (which corresponds to the setpoint imaging of the test structure 140) outside a tolerance to be defined are present, the spectacle lens 102a is defective.

To facilitate checking of the distortion of the actual imaging 142, not only the actual imaging 142 of the test structure 140 (and the image 146 of the spectacles 102 captured by the camera 112) but also a setpoint complement imaging 144 complementary to the setpoint imaging, and possibly further auxiliary structures (see FIG. 4), are displayed on the screen 116. FIGS. 1 and 4 show a crosshair as an auxiliary structure. FIG. 1 also shows part of a box 150.

The imaging 142 of the test structure 140 through the spectacle lens 102a to be tested will generally be unsharp. A sharp imaging can be achieved by the screen 110 or the spectacles holder 104 being displaced parallel to the optical axis 112a of the camera system 112, 138. The refractive power of the spectacle lens 102a (or of the spectacle lenses 102a, 102b) can thus be determined from the position of the spectacles holder 104 or the screen 110.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A method for checking the centering of a spectacle lens mounted in a spectacle frame, the method comprising:
arranging the spectacle lens in a measurement position;
providing a test structure;

capturing an actual image of the test structure with an imaging beam that passes through the spectacle lens arranged in the measurement position; and comparing at least one of:

the captured actual image with a setpoint image of the test structure which would arise for an imaging beam passing through a spectacle lens arranged in a predefined setpoint measurement position with a predefined setpoint refractive power distribution, wherein the setpoint refractive power distribution is the refractive power distribution which the spectacle lens to be checked should have computationally on account of a design data on which the spectacle lens's production is based, or the captured actual image with a setpoint complement image complementary to a setpoint image of the test structure, wherein the setpoint image of the test structure is that image which would arise for an image beam passing through a spectacle lens arranged in a predefined setpoint measurement position with a predefined setpoint refractive power distribution, wherein the setpoint refractive power distribution is the refractive power distribution which the spectacle lens to be checked should have computationally on account of the design data on which its production is based, wherein the measurement position is a predefined setpoint measurement position of the spectacle frame with regard to location and orientation.

2. The method as claimed in claim 1, wherein the test structure is calculated from the predefined setpoint image.

3. The method as claimed in claim 2, wherein the test structure is calculated from the predefined setpoint image by a light ray tracing method.

4. The method as claimed in claim 1, wherein the predefined setpoint measurement position of the spectacle frame with regard to location and orientation is determined from the coordinates of the centering point of the spectacle lens in the spectacle frame.

5. The method as claimed in claim 1, wherein at least one of:

the actual image and the setpoint image are displayed simultaneously, or the actual image and the setpoint complement image are displayed simultaneously.

6. The method as claimed in claim 5, wherein at least one of:

the actual image and the setpoint image are displayed alongside one another, the actual image and the setpoint image are displayed in a manner superimposed on one another, or the actual image and the setpoint complement image are displayed in a manner superimposed on one another.

7. The method as claimed in claim 5, wherein at least one of:

the actual image and the setpoint image are displayed in a manner brought to congruence, or the actual image and the setpoint complement image are displayed complementarily with respect to one another.

8. A device for checking the centering of a spectacle lens mounted in a spectacle frame, the device comprising:

a holder configured to arrange the spectacle lens in a measurement position;

a display unit configured to display a test structure;

an image capture unit configured to capture an actual image of the test structure for an imaging beam which passes through the spectacle lens arranged in the measurement position; and at least one of:

a comparison unit configured to compare the captured actual image with a setpoint image of the test structure, wherein the setpoint image of the test structure is that image which would arise for an imaging beam passing through a spectacle lens arranged in a predefined setpoint measurement position with a predefined setpoint refractive power distribution, wherein the setpoint refractive power distribution is the refractive power distribution which the spectacle lens to be checked should have computationally on account of the design data on which its production is based, or to compare the captured actual image with a setpoint complement image complementary to a setpoint image of the test structure, wherein the setpoint image of the test structure is that image which would arise for an imaging beam passing through a spectacle lens arranged in a predefined setpoint measurement position with a predefined setpoint refractive power distribution, wherein the setpoint refractive power distribution is the refractive power distribution which the spectacle lens to be checked should have computationally on account of the design data on which its production is based; or a display unit configured to simultaneously display the captured actual image and a setpoint image of the test structure, wherein the setpoint image of the test structure is that image which would arise for an imaging beam passing through a spectacle lens arranged in a predefined setpoint measurement position with a predefined setpoint refractive power distribution, wherein the setpoint refractive power distribution is the refractive power distribution which the spectacle lens to be checked should have computationally on account of the design data on which its production is based, or configured to simultaneously display the captured actual image and a setpoint complement image complementary to a setpoint image of the test structure, wherein the setpoint image of the test structure is that image which would arise for an imaging beam passing through a spectacle lens arranged in a predefined setpoint measurement position with a predefined setpoint refractive power distribution, wherein the setpoint refractive power distribution is the refractive power distribution which the spectacle lens to be checked should have computationally on account of the design data on which its production is based, wherein the holder is configured to hold the spectacle frame in a predefined setpoint measurement position with regard to location and orientation of the spectacle frame.

9. The device as claimed in claim 8, wherein the holder has holding points, the position of which in space is previously known.

10. The device as claimed in claim 9, wherein the holder has a compensation unit configured to compensate at least one of a forward inclination or a lateral inclination.

11. The device as claimed in claim 8, wherein the holder is configured to hold spectacles, and wherein the holder comprises an interchange unit configured to sequentially check the centering of the right and left spectacle lenses of the spectacles.

12. The device as claimed in claim 8, further comprising a displacement unit configured to displace the holder and the image capture unit relatively with respect to one another.

13. The device as claimed in claim 8, further comprising a displacement unit configured to displace the holder and the display unit configured to display the test structure relative to one another.

14. A method for checking the centering of a spectacle lens mounted in a spectacle frame, the method comprising:
arranging the spectacle lens mounted in the spectacle frame in a measurement position;
providing a test structure;
capturing an actual image of the test structure with an imaging beam which passes through the spectacle lens arranged in the measurement position;
comparing at least one of:
the captured actual image with a setpoint image of the test structure which would arise for an imaging beam passing through a spectacle lens arranged in a predefined setpoint measurement position with a predefined setpoint refractive power distribution, wherein the setpoint refractive power distribution is the refractive power distribution which the spectacle lens to be checked should have computationally on account of the design data on which its production is based, or
the captured actual image with a setpoint complement image complementary to a setpoint image of the test structure, wherein the setpoint image of the test structure is that image which would arise for an imaging beam passing through a spectacle lens arranged in a predefined setpoint measurement position with a predefined setpoint refractive power distribution, wherein the setpoint refractive power distribution is the refractive power distribution which the spectacle lens to be checked should have computationally on account of the design data on which its production is based,
wherein the measurement position is a predefined setpoint measurement position of the spectacle frame with regard to location and orientation, wherein the predefined setpoint measurement position of the spectacle frame with regard to location and orientation is determined from the coordinates of the centering point of the spectacle lens in the spectacle frame.

15. A device for checking the centering of a spectacle lens mounted in a spectacle frame, the device comprising:
a holder configured to arrange the spectacle lens mounted in the spectacle frame in a measurement position;
a display unit configured to display a test structure;
an image capture unit configured to capture an actual image of the test structure with an imaging beam which passes through the spectacle lens arranged in the measurement position; and at least one of:
a comparison unit configured to compare the captured actual image with a setpoint image of the test structure, wherein the setpoint image of the test structure is that image which would arise for an imaging beam passing through a spectacle lens arranged in a predefined setpoint measurement position with a predefined setpoint refractive power distribution, wherein the setpoint refractive power distribution is the refractive power distribution which the spectacle lens to be checked should have computationally on account of the design data on which its production is based, or to compare the captured actual image with a setpoint complement image complementary to a setpoint image of the test structure, wherein the setpoint image of the test structure is that image which would arise for an imaging beam passing through a spectacle lens arranged in a predefined setpoint measurement position with a predefined setpoint refractive power distribution, wherein the setpoint refractive power distribution is the refractive power distribution which the spectacle lens to be checked should have computationally on account of the design data on which its production is based; or
a display unit configured to simultaneously display the captured actual image and a setpoint image of the test structure, wherein the setpoint image of the test structure is that image which would arise for an imaging beam passing through a spectacle lens arranged in a predefined setpoint measurement position with a predefined setpoint refractive power distribution, wherein the setpoint refractive power distribution is the refractive power distribution which the spectacle lens to be checked should have computationally on account of the design data on which its production is based, or to simultaneously display the captured actual image and a setpoint complement image complementary to a setpoint image of the test structure, wherein the setpoint image of the test structure is that image which would arise for an imaging beam passing through a spectacle lens arranged in a predefined setpoint measurement position with a predefined setpoint refractive power distribution, wherein the setpoint refractive power distribution is the refractive power distribution which the spectacle lens to be checked should have computationally on account of the design data on which its production is based,
wherein the holder is configured to hold the spectacle frame in a predefined setpoint measurement position with regard to location and orientation, wherein the predefined setpoint measurement position of the spectacle frame with regard to location and orientation is determined from the coordinates of the centering point of the spectacle lens to be checked.

* * * * *